(12) United States Patent
Maurya et al.

(10) Patent No.: US 6,548,086 B1
(45) Date of Patent: Apr. 15, 2003

(54) **PHARMACEUTICAL COMPOSITION COMPRISING EXTRACT FROM PLANT *CRYPTOLEPIS BUCHANANI* FOR TREATING IMMUNODEFICIENCY**

(75) Inventors: Rakesh Maurya, Jammu (IN); Anpurna Kaul, Jammu (IN); Sarang Bani, Jammu (IN); Usha Zutshi, Jammu (IN); Anamika Khajuria, Jammu (IN); Ajit Kumar Saxena, Jammu (IN); Lila Ram Manahas, Jammu (IN); Ashwani Kumar, Jammu (IN); Bal Krishnan Kapahi, Jammu (IN); Om Parkash Suri, Jammu (IN); Gulam Nabi Qazi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/024,401

(22) Filed: Dec. 18, 2001

(51) Int. Cl.[7] .................. A61K 35/78; A61K 9/48; A61K 9/20; A61K 31/343; A01N 65/00

(52) U.S. Cl. .................. 424/725; 424/452; 424/465; 424/499; 514/470; 514/526

(58) Field of Search .................. 424/725, 465, 424/526, 452, 499; 514/526, 470

(56) References Cited

U.S. PATENT DOCUMENTS 5,628,999 A * 5/1997 Luo et al. .................. 424/773
5,917,052 A * 6/1999 Bierer et al. .................. 548/420

* cited by examiner

*Primary Examiner*—Herbert J. Lilling
(74) *Attorney, Agent, or Firm*—Morgan & Finnegan LLP

(57) ABSTRACT

Pharmaceutical composition and a method useful for treating immunodeficiency in animals or human beings, said composition comprising effective amount of the extract obtained from any part of plant *Cryptolepis buchanani*, either as such or its individual constituents singly or in composition with each other, optionally associated with pharmaceutically acceptable additives.

22 Claims, No Drawings

US 6,548,086 B1

PHARMACEUTICAL COMPOSITION COMPRISING EXTRACT FROM PLANT *CRYPTOLEPIS BUCHANANI* FOR TREATING IMMUNODEFICIENCY

FIELD OF THE PRESENT INVENTION

Pharmaceutical composition and a method useful for treating immunodeficiency in animals or human beings, said composition comprising effective amount of the extract obtained from any part of plant Cryptolepis buchanani, either as such or its individual constituents singly or in composition with each other, optionally associated with pharmaceutically acceptable additives

BACKGROUND AND PRIOR ART REFERENCES

*Cryptolepis buchanani* Roem. & Schult. (Family Asclepiadaceae) is distributed throughout hot deciduous forests of India and holds a very prestigious position in Ayurveda.

It is a very useful plant because of its multiple uses as a traditional medicine, such as anti-diarrheal, anti-bacterial, anti-ulcerative, anti-inflammatory, blood purifier and for lactation in women [Bhakuni, D. S., Dhar, M. L., Dhar, M. M., Dhawan, B. N., and Mehrotra, B. N., *Ind. J. Expt. Biol.,* 7: 250–262 (1969), Bhav Prakash, Commentary on Bhav Prakash Nighantu edited by C. K. Chunekar, Chowkhamba Vidya Bhavan, Varanasi 4$^{th}$ edition: 427 (1969)].

Ethanolic extract of roots and stem show hypotensive, central nervous system depressant and antiamphetaminic activity [Joshi, M. C., Patel, M. B. and Mehta, P. *J. Bull. Med. Ethno. Bot. Res.,* 1: 8–24 (1980)]. Ethanolic extract of aerial parts of plant shows diuretic activity [Dhawan, B. N., Patnaik, G. K., Rastogi, R. P., Singh, K. K. and Tandon, J. S., *Ind. J. Expt. Biol.,*15: 208–219 (1977)].

Root bark is used in rheumatic pains [Mudgal, V. and Pal, D. C., Bull. *Bot. Surv. Ind.,* 22: 59–62 (1980)]. Stem constituents are alkaloids and triterpenes, leaves constituents are α and β amyrin (Asolkar, L. V., Kakkar, K. K. and Chakre, O. J., Glossary of Indian Medicinal Plants with active principles, part-1, A–K., 1965–1981(1992)] and cryptolepine—the methyl—quinolanol alkaloid of *cryptolepis sanguinolenta.* Pyridine alkaloid, buchanine [Dutta, Sunil K, Sharma, Batuk N, Sharma, Priya V. *Phytochemistry* 17, 2047(1978)] and a cardenolide cryptosin, 7,8-Epoxy-3,11,14-trihydroxy-12-Oxocard 20 (22)-enolide [Venkateshwara R; Narendra N; Viswametra M. A; Vaidyanathan C. S.; *Phytochemistry* 28, 1203 (1989)] are the major chemical constituent of the plant. Apart from these chemical constituents cryptanoside—A to D and germenicol [Purshothman K. K; Saradha V; Connolly J. D; Rycroft D. S, *Rev. Latinomer Quim.,* 19, 28 (1988)], 1,3,6-trinicotinoyl-β-D-glucopyranoside and 1,3,6-trinicotinoyl-α-D-glucopyranoside, n-trinicontanol, n-triactonoic acid, β-amyrin and β-sitosterol glucoside [Dutta S. K; Sharma B. N; Sharma P. V., *Phytochemistry,* 17, 2047 (1978), Dutta S. K; Sharma B. N, Sharma P. V; (1980) *Phytochemistry,* 19, 1278 (1980)].

The alcoholic extract of the root shows the presence of sterols, reducing sugars and traces of glycosides and exhibited antiplatelet effects in vitro in humans, rabbits and rats. In rats, it exhibited ADP- aggregation in vitro with delayed onset and prolonged action. It exhibited an indirect fibrinolytic action in the rat possibly by causing the release of plasminogen activators from the vascular endothelium [Oyekan, A. O., Botting, J. H. and Noamesi, B. K., *General Pharmacol.,* 19: 223–227 (1988)].

A large variety of herbal drugs mentioned in Ayurveda, for their immunomodulating, adaptogenic and rejuvenating properties have been under study [Nayar, R. C. A review on the Ayurvedic drug Sariva. *J. Res. Ind. Med. Yoga. And Homoe.,* 14 (2): 69–79 (1979); Wagner, H. and Proksch, A. In progress in medicinal and aromatic plants. Research vol. 2, Eds. Farnworth, N., Hikino, H., Wagner, H., Academic Press London 1983, Labadie, R. P. Immunomodulatory compounds In: Bioactive natural products Eds. Stevan M. Colegate, Russel, J. Molyneux, CRC Press Inc., 279–317 (1993)].

These plants are believed to promote positive health and maintain organic resistance against infections by re-establishing body equilibrium and conditioning the body tissues [Bhagwandas, Fundamentals of Ayurvedic Medicine, Bansal Co., Delhi, India, ix–xvi (1978)]. Hence the drugs of plant origin are gaining increasing popularity and are being investigated for correction of immunological disorders [Aboolenein, A. A., Back to medicinal plants therapy. In the history of medicinal and aromatic plants; Proceedings of the second international congress. Alexandria, Egypt, ed. Abdallah, A., Hamdard Foundation Press, Pakistan, 40–44 (1980); Hikino, H., Recent research on oriental medicinal plants, In: Economic and Medicinal Plant Research Eds. Wagner, H., Hikino, H. and Farnsworth, N. R. (Academic Press, London): 53–85 (1985)].

Immunomodulation is a process, which alters the immune system of an organism by interfering with its functions. This interference results in either immunostimulation, an enhancement of immune reaction or immunosuppression that imply mainly to reduce resistance against infections and stress which may be because of environmental or chemotherapeutic factors [Patwardhan, B., Kulbag, D., Patki, P. S. and Nagsampagi, B. A., *Indian Drugs,* 28 (2): 56–63 (1990)]. Immunostimulation and immunosuppression both are needed to be tackled depending on the type of immunological disturbance. Recently, search for better moieties with these activities is becoming the field of major interest. Research focussed on the development of immunomodulators is directed towards activities that can be expressed in terms of stimulation or inhibition of immune factors and their integrated function [Labadie, R. P. Immunomodulatory compounds In: Bioactive natural products eds. Stevan M. Colegate, Russel, J. Molyneux, CRC Press Inc., 279–317 (1993].

Recently the understanding of research on immunomodulators has come up as a new field of immunopharmacology. Immunomodulation is a strategy for overcoming incurable autoimmune diseases involving cancer, AIDS, arthritis and allergies. An in-depth study of the immune system is supposed to provide both the theoretical and therapeutic background of many chronic disorders.

Advancement in the field of surgery, which has made organ transplantation possible, is endowed with a serious problem of organ rejection, which infact comes under the preview of immunology associated with immune system. Proper handling of this situation through modification of immune response can give new lease of life to patients with organ transplant. Delayed type hypersensitivity (DTH) and allergy manifested through altered reactivity due to previous exposure to an antigen is most of the time deleterious rather than beneficial to the individual. In the modern day life, extensive exposure to industry based pollutants/xenobiotics has resulted in emergence of a variety of immune deficiencies or hypersensitivity, situations which call for changed strategy for handling the patients, where immunology plays the pivotal role.

Keeping these emerging immunological disorders in view, major efforts have to be directed towards the formulation of new strategies, to modulate the immune responses, to permit effective treatment of various ailments associated with immune system and thus the development of a safe and effective immunomodulator for clinical use has become a major goal for many pharmaceutical investigators worldover.

Keeping in view the high reputation of *Cryptolepis buchanani* in Ayurvedic system of medicine, it was tempting to speculate that the restorative and rejuvenating power of this plant might be due to its action on immune system of the organism as no mention is made about its such effect anywhere in literature.

Liver has a pivotal role in regulation of physiological processes. Toxic chemicals and infections mainly cause liver diseases. Hepatocyte alterations of various origins result in acute and chronic dysfunctions, which may be lethal [Decker K. and Keppler D. Rev. *Physiol. Biochem. Pharmacol.*, 71, 79–106 (1974)].

Liver disorders are still the major hazard both in urban and rural population. Despite scientific advances in our understanding in the management of liver disorders and the leads provided by traditional system of medicine, no specific treatment for liver ailments is available except a few herbal preparations, WHO, Regional Office Manila, 1993.; [Subeamoniam and Pushpangadan, *Indian Journal of Pharmacology*, 31,166–175 (1999)].

It is the role of hepatoprotective agents to interfere with these pathological processes by blocking their evolution and helping recovery by preventing hepatocytes degeneration, necrosis, steatosis and inflammation, stimulate regeneration processes, and inhibit fibrosis which leads to cirrhosis and death [Doreswamy, R., Sharma, D., *Indian Drugs*, 32, 139–144 (1995)], Kumar et al, Cell injury and adaptation. In: "Basic Pathology", $5^{th}$. Edn. Prime Books (pvt.) Ltd., Banglore, India. 1992, pp. 3–24.

Acute hepatitis closely resembling viral hepatitis clinically, biochemically and histologically, can be produced by chemicals and drugs in humans and experimental animals, [A L-Tuwaijiri A. et al *Heptology*, 51: 107–113 (1981); Decker K. and Keppler D. *Rev Physiol. Biochem. Pharmacol.*, 71, 79–106 (1974); Kumar et al, Cell injury and adaptation. In: "Basic Pathology", $5^{th}$ Edn. Prime Books (Pvt.) Ltd., Banglore, India. 1992, pp. 3–24].

OBJECT OF THE PRESENT INVENTION

The main object of the present invention is to determine the role of plant *Cryptolepis buchanani* in Immune system.

Another object of the present invention is to determine the immunopotentiating activity of the said plant.

Still another object of the present invention is to determine the immunopharmacological effects of the said plant.

Still another object of the present invention is to determine the efficacy of the said plant as an immunomodulator.

Still another object of the present invention is to determine the safety profile of the said pharmaceutical composition.

Yet another object of the present invention is to determine the role of said composition in cell mediated immune response.

One more object of the present invention is to determine the role of said composition in humoral antibody response.

Still another object of the present invention is to develop a method of treating immunodeficient patients.

Still another object of the present invention is to develop a method of treating immunological disorders like AIDS, Hepatitis, Allergies, Cancer, Rheumatological disorders, etc.

Yet another object of the present invention is to develop a method of producing the extract from plant *Cryptolepis buchanani*.

SUMMARY OF THE PRESENT INVENTION

The present invention relates to Pharmaceutical composition and a method useful for treating immunodeficiency in animals or human beings, said composition comprising effective amount of the extract obtained from any part of plant *Cryptolepis buchanani*, either as such or its individual constituents singly or in composition with each other, optionally associated with pharmaceutically acceptable additives

DETAILED DESCRIPTION OF THE PRESENT INVENTION

Accordingly, the present invention relates to the development of a Pharmaceutical composition useful for treating immunodeficiency, said composition comprising effective amount of the extract obtained from any part of plant *Cryptolepis buchanani*, either as such or its individual constituents singly or in composition with each other, optionally associated with pharmaceutically acceptable additives.

In an embodiment of the present invention, the additive is selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In another embodiment of the present invention, the said composition is administered orally, inhaled, or implanted.

In yet another embodiment of the present invention, the physical state of the said composition for the oral route is in the form of capsule, tablet, syrup, concentrate, powder, granule, aerosol, or beads.

In still another embodiment of the present invention, the said composition is used for stimulating both specific and non-specific Immune reaction.

In still another embodiment of the present invention, the said composition is used for enhancing responsiveness of macrophages and subsets of T-lymphocytes and B-lymphocytes involved in antibody synthesis.

In still another embodiment of the present invention, the said composition is used for stimulating humoral response.

In still another embodiment of the present invention, the said composition shows percentage increase in the primary antibody titre ranging between 15 to 45%.

In still another embodiment of the present invention, the said composition shows percentage increase in the secondary antibody titre ranging between 10 to 25%.

In still another embodiment of the present invention, the said composition shows percentage increase in the phagocytosis ranging between 10 to 60%.

In still another embodiment of the present invention, the said composition shows percentage decrease in the graft rejection time ranging between 5 to 35%.

In still another embodiment of the present invention, the said composition shows percentage increase in the delayed type hypersensitivity response ranging between 15 to 35%.

In still another embodiment of the present invention, the said composition shows decrease in graft rejection time as statistically significant in student 't' test with P value less than 0.001.

In still another embodiment of the present invention, the said composition is used for treating animals or human beings.

In still another embodiment of the present invention, the said composition is used for treating AIDS.

In still another embodiment of the present invention, the said composition is used for treating cancer.

In still another embodiment of the present invention, the said composition is used for treating Rheumatological disorders.

In still another embodiment of the present invention, the said composition is used for treating allergies.

In still another embodiment of the present invention, the said composition is used for treating Hepatitis.

In still another embodiment of the present invention, the said composition is administered again in case of relapse conditions.

In still another embodiment of the present invention, the said composition is administered at dosage level ranging between 5 to 3000 mg/kg body weight.

In still another embodiment of the present invention, the said composition is safe for consumption and is free of any side effects.

In an embodiment of the present invention, a method of treating immunodeficiency in animals including human beings using plant *Cryptolepis buchanani* extract or a composition comprising said plant extract, optionally associated with pharmaceutically acceptable additives, said method comprising administering a pharmaceutically effective amount of said extract or composition comprising said extract to an animal including human beings suffering from immunodeficiency.

In another embodiment of the present invention, for the said method of treatment, the additive is selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In yet another embodiment of the present invention, for the said method of treatment, the additive is selected in such a manner it does not interfere with the activity of extract from *Cryptolepis buchanani*.

In still another embodiment of the present invention, for the said method of treatment, the said composition is administered orally, inhaled, or implanted.

In still another embodiment of the present invention, for the said method of treatment, the physical state of said composition for the oral route is in the form of capsule, tablet, syrup, concentrate, powder, granule, aerosol, or beads.

In still another embodiment of the present invention, for the said method of treatment, the said composition is useful for stimulating both specific and non-specific Immune reaction.

In still another embodiment of the present invention, for the said method of treatment, the said composition is useful for enhancing responsiveness of macrophages and subsets of T-lymphocytes and B-lymphocytes involved in antibody synthesis.

In still another embodiment of the present invention, for the said method of treatment, the said composition is useful for stimulating humoral response.

In still another embodiment of the present invention, for the said method of treatment, the said composition shows percentage increase in the primary antibody titre ranging between 15 to 45%.

In still another embodiment of the present invention, for the said method of treatment, the said composition shows percentage increase in the secondary antibody titre ranging between 10 to 25%.

In still another embodiment of the present invention, for the said method of treatment, the said composition shows percentage increase in the phagocytosis ranging between 10 to 60%.

In still another embodiment of the present invention, for the said method of treatment, the said composition shows percentage decrease in the graft rejection time ranging between 5 to 35%.

In still another embodiment of the present invention, for the said method of treatment, the said composition shows percentage increase in the delayed type hypersensitivity response ranging between 15 to 35%.

In still another embodiment of the present invention, for the said method of treatment, the said composition shows decrease in graft rejection time as statistically significant in student 't' test with P value less than 0.001.

In still another embodiment of the present invention, the said method is useful for treating AIDS.

In still another embodiment of the present invention, the said method is useful for treating cancer.

In still another embodiment of the present invention, the said method is useful for treating Rheumatological disorders.

In still another embodiment of the present invention, the said method is useful for treating allergies.

In still another embodiment of the present invention, the said method is useful for treating Hepatitis.

In still another embodiment of the present invention, for the said method of treatment, the said composition is administered again in case of relapse conditions.

In still another embodiment of the present invention, for the said method of treatment, the said composition is administered at dosage level ranging between 5 to 3000 mg/kg body weight.

In still another embodiment of the present invention, for the said method of treatment, the said composition is safe for consumption and is free of any side effects.

In an embodiment of the present invention, a method of producing an extract from Plant *Cryptolepis buchanani,* useful for treating immunodeficiency, said extract comprising effective amount of the extract obtained from any part of plant *Cryptolepis buchanani,* either as such or its individual constituents singly or in combination with each other, optionally associated with pharmaceutically acceptable additives.

In another embodiment of the present invention, powdering the said plant material.

In yet another embodiment of the present invention, extracting the powdered plant material by cold percolation.

In still another embodiment of the present invention, concentrating the percolated extract.

In still another embodiment of the present invention, triturating the concentrated extract successively with organic solvents of increasing polarity.

In still another embodiment of the present invention, separating the components by conventional methods.

In still another embodiment of the present invention, the solvents used for the extraction are selected from a group comprising rectified spirit, aqueous spirit, water, and methanol.

In still another embodiment of the present invention, the organic solvents used for trituration are selected from a group comprising hexane, chloroform, and ethyl acetate.

The present invention relates to immunomodulating activity of an extract from *Cryptolepis buchanani*.

In still another embodiment of the present invention, immunomodulating activity of an extract from *Cryptolepis buchanani*, standardised on the basis of two compounds isolated from the extract, having the formula (1 and 2) as shown:

Formula 1

Formula 2

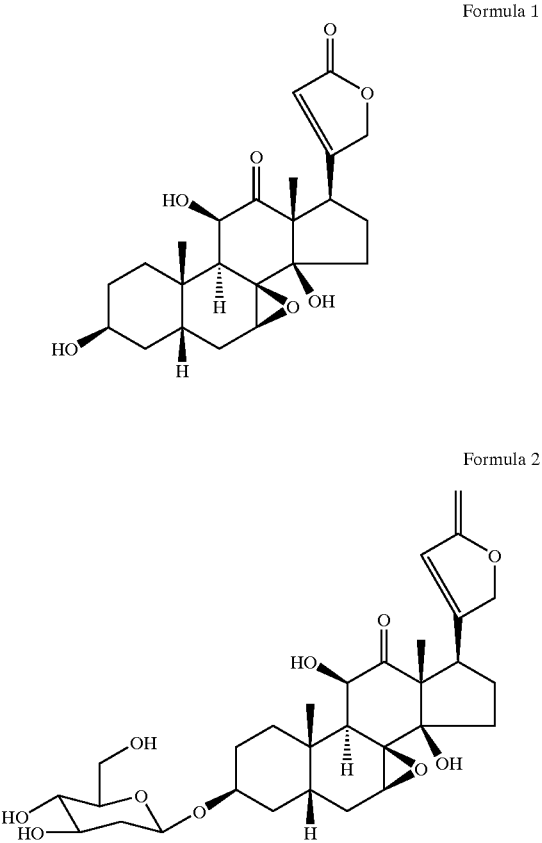

by extracting powdered roots, aerial part, whole plant, in a polar solvent like rectified spirit, methanol, aqueous rectified spirit, water in glass percolator, removing fatty nonpolar constituents by triturating with hexane, dichloromethane, chloroform or ethyl acetate, to get fraction for isolation of compounds.

In still another embodiment of the present invention, the plant material is powdered by conventional methods.

In still another embodiment of the present invention, the alcoholic extract of the plant material is prepared by cold percolation using propanol, methanol, ethanol, or n-butanol.

In still another embodiment of the present invention, the alcoholic extract (A001) is concentrated by conventional method.

In still another embodiment of the present invention, successive trituration i.e., shaking the extract with the solvent] is done using the alcoholic extract with hexane, and chloroform to get hexane soluble fraction (F001) and chloroform soluble fraction (F002) and residue.

In still another embodiment of the present invention, residue obtained as above is suspended in water.

In still another embodiment of the present invention, the fraction is then extracted with n-butanol, to furnish n-butanol soluble fraction (F003), In still another embodiment of the present invention, compounds from n-butanol soluble fraction (F003) is isolated by column chromatography, furnished 1 (30 mg) and 2 (50 mg), In still another embodiment of the present invention, compound 1 obtained as crystalline compound.

In still another embodiment of the present invention, melting point of compound 1 is 195–196° C.

In still another embodiment of the present invention, the molecular formula of compound 1 is $C_{23}H_{30}O_7$.

In still another embodiment of the present invention, UV spectrum of compound 1 is recorded in methanol shows absorption maxima at 224 nm.

In still another embodiment of the present invention, IR (KBr) spectrum of compound 1 shows absorptions at 3400, 2900, 1730, 1708, and 1640 $cm^{-1}$.

In still another embodiment of the present invention, $^1H$ NMR of compound 1 (200.13 MHz, $CDCl_3$) showed signals at δ6.01 (1H, s), 4.82 (1H, dd, J=4.1, 1.6 Hz), 4.70 (1H, dd, J=4.1, 12.7 Hz), 4.08 (1H, brs), 3.92 (1H, t, J=8.3 Hz), 3.63 (1H, d, J=4.1Hz), 3.38 (1H, d, J=6.3 Hz), 2.70 (1H, d, J=2.2 Hz), 1.25 (3H, s), 1.07 (3H,s).

In still another embodiment of the present invention, the $^{13}C$ NMR spectrum of compound 1 shows signals at δ212.9, 175.7, 174.0, 117.9, 81.6, 74.5, 74.3, 65.8, 64.3, 63.3, 52.3, 42.5, 36.0, 35.8, 35.0, 34.8, 32.2, 28.5, 28.1, 27.2, 22.8, 17.7.

In still another embodiment of the present invention, electron induced mass spectrum (EIMS m/z) of compound 1 is 419 $[M+H]^+$.

In still another embodiment of the present invention, compound 2 is obtained as crystalline compound, In still another embodiment of the present invention, melting point of compound 2 is 225–230° C., In still another embodiment of the present invention, Molecular formula of compound 2 is $C_{29}H_{40}O_{11}$.

In still another embodiment of the present invention, UV spectrum of compound 2 recorded in chloroform shows absorption maxima at 239, 275 nm.

In still another embodiment of the present invention, IR (KBr) spectrum of compound 2 is shows absorption at 3300, 2900, 1730, 1710, and 1630 $cm^{-1}$.

In still another embodiment of the present invention, $^1H$ NMR of compound 2 (200.13 MHz, $CDCl_3$) shows signals at δ6.01 (1H, s), 4.90 (4H, m), 4.70 (1H, d, J 12.8 Hz), 3.00–4.00 (sugar protons), 3.41 (2H, s), 1.23 (3H, s), 1.07 (3H, s).

In still another embodiment of the present invention, The $^{13}C$ NMR spectrum of compound 2 also shows signals at δ213.4, 174.2, 170.9, 119.2, 95.9, 81.6, 78.7, 77.6, 76.6, 74.1, 74.0, 70.9, 68.1, 63.6, 63.1, 56.8, 52.9, 42.8, 36.2, 36.1, 35.1, 34.9, 32.9, 28.9, 27.4, 27.3, 23.6, 18.7, 18.1.

In still another embodiment of the present invention, fast atom bombardment mass spectrum (FABMS m/z) of compound 2 is 564 $[M^+]$.

In still another embodiment of the present invention, ethanolic, 50% ethanolic and aqueous extract of the root of *Cryptolepis buchanani* on submitting to preliminary immunopharmacological screening show significant immunopotentiating activity.

In still another object of the present invention, ethanolic extract is the most active and therefore, a detailed study of ethanolic extract is undertaken to establish its activity against various parameters that are related to the immunopotentiating activity.

In still another embodiment of the present invention, an initial acute toxicity study is carried out and no mortality or any change in normal general behaviour is observed upto the dose as high as 3000 mg/kg orally administered in both rats and mice.

In still another embodiment of the present invention, no untoward symptom is observed over one week period of study in these experimental animals.

In still another embodiment of the present invention, ethanolic extract produce a dose related increase in SRBC induced DTH reaction which shows the stimulatory effect on 'T' lymphocytes.

In still another embodiment of the present invention, evidence leading to support the hypothesis of T-lymphocytes stimulation by DTH reaction is the earlier rejection of the homologous skin graft rejection in mice when compared to untreated control.

In still another embodiment of the present invention, the mechanism involved in reduction in graft rejection time is the stimulation of T-lymphocytes. This shows immunostimulatory activity of ethanolic extract.

In still another embodiment of the present invention, the stimulation of humoral response against sheep red blood cells (SRBC) by ethanolic extract indicate enhanced responsiveness of macrophages and subsets of T and B-lymphocytes, involved in antibody synthesis.

In still another embodiment of the present invention, macrophages coordinate the processing and presentation of antigen to T and B cells and the increase of humoral response to SRBC reveal that ethanolic extract is acting by augmenting these processes.

In still another embodiment of the present invention, quick clearance of carbon particles through reticuloendothelial system by the process of phagocytosis also suggest enhanced functioning of macrophages with ethanolic extract by causing stimulation of non-specific immune response.

In still another embodiment of the present invention, all these findings suggest that ethanolic extract have a significant immunostimulant activity that is suggestive of its possible usefulness as a therapeutic agent in immune compromised patients.

In still another embodiment of the present invention, plant *Cryptolepis buchanani* is a source potent immunostimulant, capable of stimulating both specific and non-specific mechanisms.

In still another embodiment of the present invention, plant *Cryptolepis buchanani* increase the humoral antibody synthesis and exhibit potential DTH reaction enhancing properties.

In still another embodiment of the present invention, plant *Cryptolepis buchanani* cause marked reduction in graft rejection time (GRT).

In still another embodiment of the present invention, plant *Cryptolepis buchanani* increase the Phagocytic function of reticulo-endothelial system.

In still another embodiment of the present invention, plant *Cryptolepis buchanani* is a suitable candidate with its immunopharmacological effects, providing the basis for extending its use in immunodeficient state associated with cancer, AIDS and rheumatism.

In still another embodiment of the present invention, plant *Cryptolepis buchanani* can be used as an immune modifier in combination therapy.

The invention is described in detail by the examples given below which should not be construed to the limit of scope of the present invention.

EXAMPLE 1

The shade dried, powdered *Cryptolepis buchanani* roots (0.5 kg) were extracted with rectified spirit by cold percolation (5×16 hours). The rectified spirit was evaporated under reduced pressure to obtain a brown mass; this was submitted for immunomodulating activity, further this extract was triturated successively with hexane, chloroform and ethyl acetate. The residue left was dissolved in water, and extracted with n-butanol, the n-butanol soluble portion was subjected for the isolation of compounds by column chromatography over silica gel (230 400 mesh), column was eluted with mixture of chloroform-methanol (19:1), furnished 1 (30 mg, 0.006%) and 2 (50 mg, 0.01%).

TABLE 1

Comparative study of extracts at 100-mg/kg p.o. humoral antibody titre (Primary & Secondary), delayed type hypersensity response, phagocytic and graft rejection time.

| Nature of extract | % Change in Humoral antibody titre Days + 7 Primary | % Change in Humoral antibody titre Days + 14 Secondary | DTH response (mm) 24 hr. | Phyagocytic % change | GRT % change |
| --- | --- | --- | --- | --- | --- |
| EtOH | +40.83 | +23.52 | +30.35 | +54.60 | −30.43 |
| EtOH:H$_2$O (1:1) | +20.00 | +12.50 | 23.50 | +21.71 | −14.78 |
| H$_2$O | +17.64 | +11.42 | +19.28 | +13.88 | −6.94 |

Effect on Humoral Immune Response

This extract showed 16.66 to 40.83% increase in the primary antibody titre and 8.82 to 23.52 in secondary antibody titre (Table 1) from 25 to 100 mg/kg per oral dose range for seven days in experimental mice.

Effect on Delayed Type Hypersensitivity (DTH) Response

This extract was studied at 25, 50 and 100 mg/kg p.o. administration for 7 days in mice for DTH response. It showed highly significant values from 14.28 to 30.35% at the above said dose levels (Table 1).

Effect on Phagocytic Index (K)

Oral administration of ethanolic extract at 100 mg/kg for 7 days enhanced the phagocytic function of reticuloendothelial system, resulting in significant increase by 54.60% (Table 1).

Effect on Graft Rejection Time

This extract on oral administration of 100 mg/kg dose for 7 days hastened the graft rejection by 30–43% (Table 1) with values significant statistically [($P<0.01$) students 't' test].

EXAMPLE 2

The shade dried, powdered *Cryptolepis buchanani* roots (0.5 kg) were extracted with rectified spirit: water (1:1) by cold percolation (5×16 hours). The solvent was evaporated under reduced pressure to obtain a brown mass and this was submitted for immunomodulating activity.

Effect on Humoral Immune Response

Effect of 50% ethanolic extract of *Cryptolepis buchanani* demonstrated dose related increase in primary. and secondary antibody titre (9.23 to 20.00% and 5.55 to 12.50%) in experimental animals (Table 1)).

Effect on Delayed Type Hypersensitivity (DTH) Response

Effect of 50% ethanolic extract of *Cryptolepis buchanani* produced dose dependent increase in DTH response ranging between 10.62 to 23.50% (Table 1) when administered orally for 7 days in mice.

Effect on Phagocytic Index (K)

Oral administration of ethanolic extract at 100 mg/kg for 7 days enhanced the phagocytic function of reticuloendothelial system, resulting in increase by 21.71% (Table 1).

Effect on Graft Rejection Time

This extract on oral administration of 100 mg/kg dose for 7 days hastened the graft rejection, while reducing the graft rejection time by 14.78% (Table 1).

EXAMPLE 3

The shade dried, powdered *Cryptolepis buchanani* roots (0.5 kg) was heated with water (1:8 W: V) on water bath (5×4 hours). The solvent was evaporated under reduced pressure to obtain a brown mass; this was submitted for immunomodulating activity.

Effect on Humoral Immune Response

Aqueous extract of *Cryptolepis buchanani,* was studied against SRBC induced humoral antibody response. This extract produced dose-related increase in primary and secondary antibody production (8.82 to 17.64 and 4.28 to 11.42%) at dose range of 25–100 mg/kg when administered in mice orally for 7 days (Table 1).

Effect on Delayed Type Hypersensitivity (DTH) Response

Dose related increase in the DTH response was observed at 25, 50 and 100 mg/kg administered per oral for 7 days. The percent increase in DTH response was found to be in the range of 7.14 to 19.38% (Table 1). The values were significant at 50 and 100 mg/kg i.e. P<0.01 and <0.001 respectively (students 't' test).

Effect on Phagocytic Index (K)

Oral administration of ethanolic extract at 100 mg/kg for 7 days enhanced the phagocytic function of reticuloendothelial system, resulting in increase by 13.88% (Table 1).

Effect on Graft Rejection Time

This extract on oral administration of 100 mg/kg dose for 7 days hastened the graft rejection, while reducing the graft rejection time by 6.94% (Table 1).

What is claimed is:

1. A method of treating immunodeficiency in animals including human beings using plant *Cryptolepis buchanani* extract or a composition comprising said plant extract, optionally associated with pharmaceutically acceptable additives, said method comprising administering to an animal, including human beings, suffering from immunodeficiency a pharmaceutically effective amount of said extract or composition comprising said extract, wherein the extract contains the following two chemical compounds:

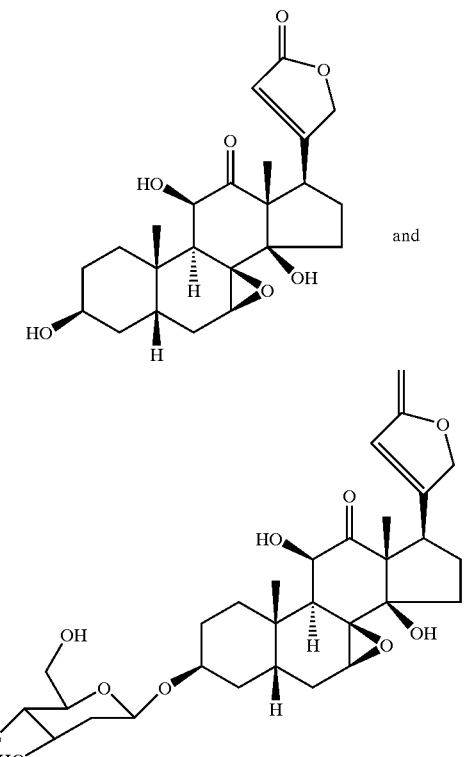

and

2. A method as claimed in claim 1 wherein, the additive is selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

3. A method as claimed in claim 1 wherein, the additive is selected in such a manner it does not interfere with the activity of extract from *Cryptolepis buchanani*.

4. A method as claimed in claim 1 wherein, said composition is administered orally, inhaled, or implanted.

5. A method as claimed in claim 1 wherein, physical state of said composition for the oral route is in the form of capsule, tablet, syrup, concentrate, powder, granule, aerosol, or beads.

6. A method as claimed in claim 1 wherein, said composition is useful for stimulating both specific and non-specific Immune reaction.

7. A method as claimed in claim 6 wherein, said composition is useful for enhancing responsiveness of macrophages and subsets of T-lymphocytes and B-lymphocytes involved in antibody synthesis.

8. A method as claimed in claim 6 wherein, said composition is useful for stimulating humoral response.

9. A method as claimed in claim 6 wherein, said composition shows percentage increase in the primary antibody titre ranging between 15 to 45%.

10. A method as claimed in claim 6 wherein, said composition shows percentage increase in the secondary antibody titre ranging between 10 to 25%.

11. A method as claimed in claim 6 wherein, said composition shows percentage increase in the phagocytosis ranging between 10 to 60%.

12. A method as claimed in claim 6 wherein, said composition shows percentage decrease in the graft rejection time ranging between 5 to 35%.

13. A method as claimed in claim 6 wherein, said composition shows percentage increase in the delayed type hypersensitivity response ranging between 15 to 35%.

14. A method as claimed in claim 6 wherein, said composition shows decrease in graft rejection time as statistically significant in student 't' test with P value less than 0.001.

15. A method as claimed in claim 1 is useful for treating AIDS.

16. A method as claimed in claim 1 is useful for treating cancer.

17. A method as claimed in claim 1 is useful for treating Rheumatological disorders.

18. A method as claimed in claim 1 is useful for treating allergies.

19. A method as claimed in claim 1 is useful for treating Hepatitis.

20. A method as claimed in claim 1 wherein, said composition is administered again in case of relapse conditions.

21. A method as claimed in claim 1 wherein, said composition is administered at dosage level ranging between 5 to 3000 mg/kg body weight.

22. A method as claimed in claim 1 wherein, said composition is safe for consumption and is free of any side effects.

* * * * *